United States Patent [19]

Fujimura et al.

[11] Patent Number: 5,578,456
[45] Date of Patent: Nov. 26, 1996

[54] ANTI-TREPONEMA PALLIDUM ANTIBODY IMMUNOASSAY

[75] Inventors: Katsuya Fujimura; Eiichi Ueno; Nobuyuki Fujii; Masahisa Okada, all of Tokyo, Japan

[73] Assignee: Fujirebio Inc., Japan

[21] Appl. No.: 395,507

[22] Filed: Feb. 27, 1995

[51] Int. Cl.[6] .................................................. G01N 33/571
[52] U.S. Cl. .................... 435/7.36; 435/69.3; 424/262.1; 436/811
[58] Field of Search ...................... 435/7.36, 69.3; 424/262.1; 436/811; 530/388.4, 825

[56] References Cited

U.S. PATENT DOCUMENTS

| | | | |
|---|---|---|---|
| 4,618,588 | 10/1986 | Sato et al. | 435/7.36 |
| 5,364,774 | 11/1994 | Muir et al. | 435/69.3 |

FOREIGN PATENT DOCUMENTS

0079145A1  5/1983  European Pat. Off. .
0154916A2  9/1985  European Pat. Off. .

OTHER PUBLICATIONS

Weigel et al., Analysis of the N–Terminal Region of the 47–Kilodalton Integral Membrane Lipoprotein of Treponema pallidum, Infection and Immunity, vol. 60, No. 4 (1992), pp. 1568–1576.
Smith et al. Gene 67:31–40 (1988).
Purcell et al. Mol. Microbiol. 4(8):1371–1379 (1990).
Byrne et al. J. Clin. Microbiol. 30(1):115–122 (1992).
Akins et al. Infect. Immun. 61(4):1202–1210 (1993).
Stamm et al. Infect Immun 62(1):271–279 (1994).

*Primary Examiner*—James C. Housel
*Assistant Examiner*—Gary Tanigawa
*Attorney, Agent, or Firm*—Pollock, Vande Sande & Priddy

[57] ABSTRACT

A new method for assaying anti-*Treponema pallidum* antibody with improved sensitivity is provided. Anti-Tp antibody in serum is assayed by enzyme immunoanalysis utilizing the antigen-antibody reaction between G15 and/or G17 antigen, a protein available on fusion of GST to the N-terminal of a Tp membrane antigen (15 and/or 17 kDa), and anti-Tp antibody in a sample.

12 Claims, 7 Drawing Sheets

5,578,456

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 352 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: rabbit ( i x ) FEATURE:
        ( A ) NAME/KEY: Protein
        ( B ) LOCATION: 1..352
        ( D ) OTHER INFORMATION: /note="G15 Antigen"

( x i ) SEQUENCE DESCRIPTION: SEQ ID NO:1:

```
Met  Ser  Pro  Ile  Leu  Gly  Tyr  Trp  Lys  Ile  Lys  Gly  Leu  Val  Gln  Pro
 1              5                   10                      15

Thr  Arg  Leu  Leu  Leu  Glu  Tyr  Leu  Glu  Glu  Lys  Tyr  Glu  Glu  His  Leu
              20                   25                      30

Tyr  Glu  Arg  Asp  Glu  Gly  Asp  Lys  Trp  Arg  Asn  Lys  Lys  Phe  Glu  Leu
              35                   40                      45

Gly  Leu  Glu  Phe  Pro  Asn  Leu  Pro  Tyr  Tyr  Ile  Asp  Gly  Asp  Val  Lys
              50                   55                      60

Leu  Thr  Gln  Ser  Met  Ala  Ile  Ile  Arg  Tyr  Ile  Ala  Asp  Lys  His  Asn
 65                   70                       75                          80

Met  Leu  Gly  Gly  Cys  Pro  Lys  Glu  Arg  Ala  Glu  Ile  Ser  Met  Leu  Glu
              85                   90                       95

Gly  Ala  Val  Leu  Asp  Ile  Arg  Tyr  Gly  Val  Ser  Arg  Ile  Ala  Tyr  Ser
              100                  105                     110

Lys  Asp  Phe  Glu  Thr  Leu  Lys  Val  Asp  Phe  Leu  Ser  Lys  Leu  Pro  Glu
              115                  120                     125

Met  Leu  Lys  Met  Phe  Glu  Asp  Arg  Leu  Cys  His  Lys  Thr  Tyr  Leu  Asn
              130                  135                     140

Gly  Asp  His  Val  Thr  His  Pro  Asp  Phe  Met  Leu  Tyr  Asp  Ala  Leu  Asp
145                        150                     155                     160

Val  Val  Leu  Tyr  Met  Asp  Pro  Met  Cys  Leu  Asp  Ala  Phe  Pro  Lys  Leu
                   165                  170                     175

Val  Cys  Phe  Lys  Lys  Arg  Ile  Glu  Ala  Ile  Pro  Gln  Ile  Asp  Lys  Tyr
              180                       185                     190

Leu  Lys  Ser  Ser  Lys  Tyr  Ile  Ala  Trp  Pro  Leu  Gln  Gly  Trp  Gln  Ala
              195                       200                     205

Thr  Phe  Gly  Gly  Gly  Asp  His  Pro  Pro  Lys  Ser  Asp  Leu  Val  Pro  Arg
         210                      215                     220

Gly  Ser  Glu  Leu  Cys  Ser  Phe  Ser  Ser  Ile  Pro  Asn  Gly  Thr  Tyr  Arg
225                      230                      235                     240
```

```
Ala  Thr  Tyr  Gln  Asp  Phe  Asp  Glu  Asn  Gly  Trp  Lys  Asp  Phe  Leu  Glu
                    245                      250                      255

Val  Thr  Phe  Asp  Gly  Gly  Lys  Met  Val  Gln  Val  Val  Tyr  Asp  Tyr  Gln
                    260                      265                      270

His  Lys  Glu  Gly  Arg  Phe  Lys  Ser  Gln  Asp  Ala  Asp  Tyr  His  Arg  Val
          275                      280                      285

Met  Tyr  Ala  Ser  Ser  Gly  Ile  Gly  Pro  Glu  Lys  Ala  Phe  Arg  Glu  Leu
          290                      295                      300

Ala  Asp  Ala  Leu  Leu  Glu  Lys  Gly  Asn  Pro  Glu  Met  Val  Asp  Val  Val
305                           310                      315                      320

Thr  Gly  Ala  Thr  Val  Ser  Ser  Gln  Ser  Phe  Arg  Arg  Leu  Gly  Arg  Ala
                    325                      330                      335

Leu  Leu  Gln  Ser  Ala  Arg  Arg  Gly  Glu  Lys  Glu  Ala  Ile  Ile  Ser  Arg
                    340                      345                      350
```

( 2 ) INFORMATION FOR SEQ ID NO:2:

( i ) SEQUENCE CHARACTERISTICS:
        ( A ) LENGTH: 362 amino acids
        ( B ) TYPE: amino acid
        ( C ) STRANDEDNESS:
        ( D ) TOPOLOGY: Not Relevant ( i i ) MOLECULE TYPE: protein ( i i i ) HYPOTHETICAL: NO ( i v ) ANTI-SENSE: NO ( i x ) FEATURE:
        ( A ) NAME/KEY: Protein
        ( B ) LOCATION: 1..362
        ( D ) OTHER INFORMATION: /note="G17 Antigen"

( x i ) SEQUENCE DESCRIPTION: SEQ ID NO:2:

```
Met  Ser  Pro  Ile  Leu  Gly  Tyr  Trp  Lys  Ile  Lys  Gly  Leu  Val  Gln  Pro
1                   5                        10                       15

Thr  Arg  Leu  Leu  Leu  Glu  Tyr  Leu  Glu  Glu  Lys  Tyr  Glu  Glu  His  Leu
                    20                       25                       30

Tyr  Glu  Arg  Asp  Glu  Gly  Asp  Lys  Trp  Arg  Asn  Lys  Lys  Phe  Glu  Leu
          35                       40                       45

Gly  Leu  Glu  Phe  Pro  Asn  Leu  Pro  Tyr  Tyr  Ile  Asp  Gly  Asp  Val  Lys
     50                       55                       60

Leu  Thr  Gln  Ser  Met  Ala  Ile  Ile  Arg  Tyr  Ile  Ala  Asp  Lys  His  Asn
65                       70                       75                       80

Met  Leu  Gly  Gly  Cys  Pro  Lys  Glu  Arg  Ala  Glu  Ile  Ser  Met  Leu  Glu
                    85                       90                       95

Gly  Ala  Val  Leu  Asp  Ile  Arg  Tyr  Gly  Val  Ser  Arg  Ile  Ala  Tyr  Ser
                    100                      105                      110

Lys  Asp  Phe  Glu  Thr  Leu  Lys  Val  Asp  Phe  Leu  Ser  Lys  Leu  Pro  Glu
          115                      120                      125

Met  Leu  Lys  Met  Phe  Glu  Asp  Arg  Leu  Cys  His  Lys  Thr  Tyr  Leu  Asn
          130                      135                      140

Gly  Asp  His  Val  Thr  His  Pro  Asp  Phe  Met  Leu  Tyr  Asp  Ala  Leu  Asp
145                      150                      155                      160

Val  Val  Leu  Tyr  Met  Asp  Pro  Met  Cys  Leu  Asp  Ala  Phe  Pro  Lys  Leu
                    165                      170                      175

Val  Cys  Phe  Lys  Lys  Arg  Ile  Glu  Ala  Ile  Pro  Gln  Ile  Asp  Lys  Tyr
                    180                      185                      190
```

| | | | | | | | | | | | | | | |
|---|---|---|---|---|---|---|---|---|---|---|---|---|---|---|
| Leu | Lys | Ser 195 | Ser | Lys | Tyr | Ile | Ala 200 | Trp | Pro | Leu | Gln | Gly 205 | Trp | Gln | Ala |
| Thr | Phe 210 | Gly | Gly | Gly | Asp | His 215 | Pro | Pro | Lys | Ser | Asp 220 | Leu | Val | Pro | Arg |
| Gly 225 | Ser | Glu | Leu | Val | Ser 230 | Cys | Thr | Thr | Val | Cys 235 | Pro | His | Ala | Gly | Lys 240 |
| Ala | Lys | Ala | Glu | Lys 245 | Val | Glu | Cys | Ala | Leu 250 | Lys | Gly | Gly | Ile | Phe 255 | Arg |
| Gly | Thr | Leu | Pro 260 | Ala | Ala | Asp | Cys | Pro 265 | Gly | Ile | Asp | Thr | Thr 270 | Val | Thr |
| Phe | Asn | Ala 275 | Asp | Gly | Thr | Ala | Gln 280 | Lys | Val | Glu | Leu | Ala 285 | Leu | Glu | Lys |
| Lys | Ser 290 | Ala | Pro | Ser | Pro | Leu 295 | Thr | Tyr | Arg | Gly | Thr 300 | Trp | Met | Val | Arg |
| Glu 305 | Asp | Gly | Ile | Val | Glu 310 | Leu | Ser | Leu | Val | Ser 315 | Ser | Glu | Gln | Ser | Lys 320 |
| Ala | Pro | His | Glu | Lys 325 | Glu | Leu | Tyr | Glu | Leu 330 | Ile | Asp | Ser | Asn | Ser 335 | Val |
| Arg | Tyr | Met | Gly 340 | Ala | Pro | Gly | Ala | Gly 345 | Lys | Pro | Ser | Lys | Glu 350 | Met | Ala |
| Pro | Phe | Tyr 355 | Val | Leu | Lys | Lys | Thr 360 | Lys | Lys | | | | | | |

ANTI-TREPONEMA PALLIDUM ANTIBODY IMMUNOASSAY

FIELD OF THE INVENTION

This invention relates to a method for detection and assay of anti-*Treponema pallidum* antibody.

BACKGROUND OF THE INVENTION

Syphilis is a disease caused by *Treponema pallidum* (hereinafter sometimes referred to briefly as Tp). The diagnosis of syphilis is generally made by an immunoassay of anti-Tp antibody in the blood. The surface of Tp cell has a large number of membrane antigens and the above mentioned immunoassay utilizes the antigen-antibody reaction between the membrane antigen and the anti-Tp antibody in a blood specimen. The Tp membrane antigen for use in the immunoassay today is prepared by innoculating Tp into rabbit testis and disrupting the harvested viable cells. However, since Tp is cultured using rabbit testis, the sensitivity and reproducibility of this assay are low owing to contamination with impurities and, it is difficult to provide a large quantity of Tp.

To overcome these disadvantages, it has been proposed to clone a gene coding for the Tp membrane antigen, mass-produce said membrane antigen by biotechnology and use it in the above mentioned immunoassay. For example, Japanese Kohyo publication Hei-2-500403 describes a technology which comprises preparing a Tp antigen having a molecular weight (MW) of 47 kDa by biotechnology and assaying the anti-Tp antibody immunologically using this antigen.

The technology disclosed in Japanese Kohyo publication Hei-2-500403 enables the immunoassay of anti-Tp antibody, but it would benefit the diagnosis of syphilis should the anti-Tp antibody be assayed with improved sensitivity.

Therefore, this invention has for its object to provide a method for assay of anti-Tp antibody which enables the assay of anti-Tp antibody with improved sensitivity as compared with the conventional method.

SUMMARY OF THE INVENTION

The inventors of this invention did much research and found that when G15 antigen and/or G17 antigen which is available on fusion of glutathione-S-transferase (GST) to the N-terminal of a MW 15 kDa or 17 kDa antigen, among Tp membrane antigens, is used as the assay antigen, anti-Tp antibody can be assayed with a significantly higher sensitivity than the sensitivity of the conventional method.

Thus, this invention provides a method for assay of anti-Tp antibody which comprises quantitating anti-Tp antibody in a sample utilizing the antigen-antibody reaction between either G15 antigen, which is a protein available on fusion of GST to the N-terminal of a Tp membrane antigen having a molecular weight of 15 kDa, and/or G17 antigen, which is a protein available on fusion of GST to the N-terminal of a Tp membrane antigen having a molecular weight of 17 kDa, and said anti-Tp antibody in a sample.

DETAILED DESCRIPTION OF THE INVENTION

This invention is now described in detail.

It is known that antigens having various molecular weights are present on the surface of Tp cell, and as representative species, antigens having molecular weights of 47 kDa, 42 kDa, 17 kDa and 15 kDa, respectively, are known. These antigens are distinguishable from one another electrophoretically (Journal of Immunology, Vol. 129, pp.1287–1291, 1982; Journal of Clinical Microbiology, Vol. 21, pp. 82–87, 1985; Journal of Clinical Microbiology, Vol. 30, pp.115–122, 1992). In addition to the gene coding for the membrane antigen having a molecular weight of 47 kDa, genes coding for membrane antigens having molecular weights of 17 kDa and 15 kDa have already been cloned and produced by biotechnology. Furthermore, their amino acid sequences have also been established (INFECTION AND IMMUNITY, Vol. 57, No. 12, pp.3708–3714, 1989; Molecular Microbiology (1990) 4(8), 1371–1379; INFECTION AND IMMUNITY, Vol. 61, No. 4 pp.1202–1210, 1993).

The antigen for use in accordance with this invention is a fused protein (G15 antigen) available on fusion of GST to the N-terminal of the above mentioned Tp membrane antigen having a molecular weight of 15 kDa, and/or a fused protein (G17 antigen) available on fusion of GST to the N-terminal of the above mentioned Tp membrane antigen having a molecular weight of 17 kDa. GST fused proteins as such and the biotechnology of their production are already known (INFECTION AND IMMUNITY, Apr. 1993, pp.1202–1210). However, the inventors of this invention should be credited with the surprising discovery that the sensitivity of the immunoassay of anti-Tp antibody is significantly enhanced when either G15 or G17, or both, are used in lieu of the membrane antigens not linked to GST.

Figure 1:
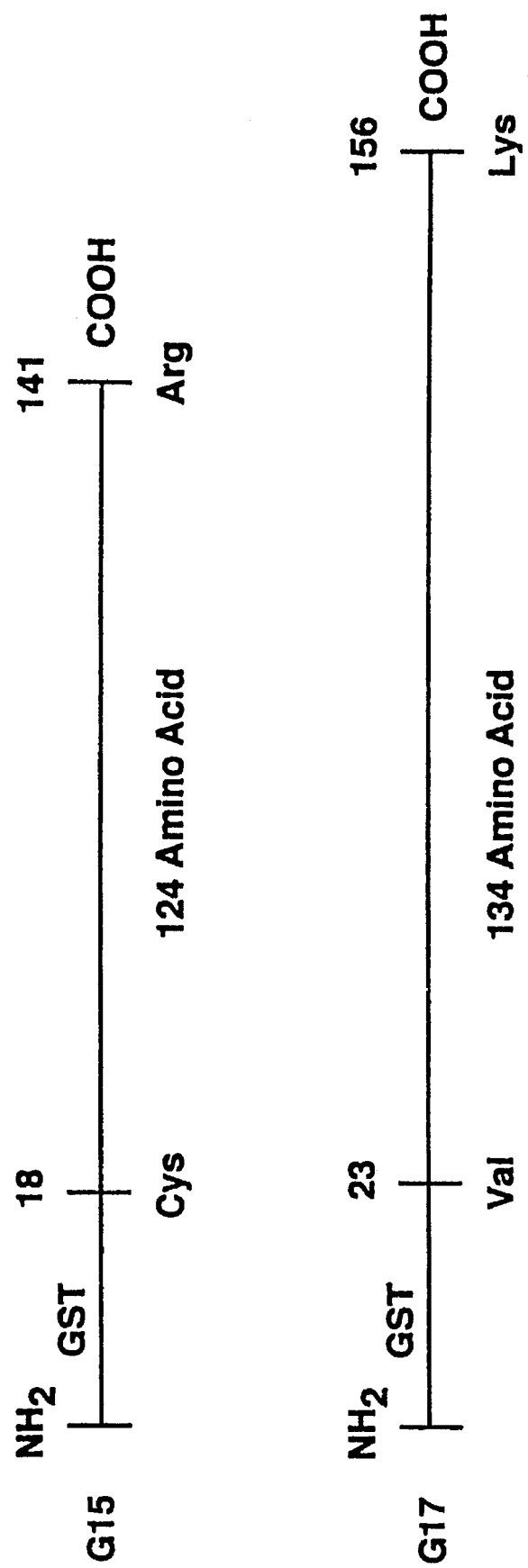
FIG. 1 is a diagrammatic representation of the structures of G15 and G17 antigens for use in the method of this invention.

The structures of G15 and G17 antigens for use in the practice of this invention are shown in FIG. 1. While these G15 and G17 antigens can be prepared by the methods described in the above mentioned literature, the preferred procedures are described in detail in the examples which appear hereinafter.

The method of this invention is a method for immunoassay of anti-Tp antibody utilizing the antigen-antibody reaction between either said G15 antigen or said G17 antigen, or both, and anti-Tp antibody in a sample. A variety of immunoassay procedures are known to those skilled in the art and any of such known procedures can be utilized in the practice of this invention. Thus, classified by reaction pattern, the sandwich method and the agglutination test, among others, can be utilized. Classified by label, the enzyme immunoanalysis, immunofluorescence analysis and radio immunoanalysis, among others, can be mentioned. Of these methods, the sandwich method (sandwich ELISA) which does not require large-scale equipment and is simple procedure-wise, sufficiently sensitive, and suited for the analysis of multiple samples is the most preferred. For the determination of human anti-Tp antibody, for instance, G15 antigen or G17 antigen, or both, are immobilized in the wells of a 96-well microtiter plate. After blocking the non-specific adhesion sites, the wells are washed and the test sample is added for reaction. The wells are washed and an enzyme (e.g. peroxidase)-labeled anti-human immunoglobulin antibody is added for reaction. The plate is washed and the substrate for the conjugated enzyme is added for enzymatic reaction and color development. After the reaction is stopped, the intensity of the developed color is assessed spectrometrically to quantitate the anti-Tp antibody in the sample. The sandwich ELISA itself is well known in this field and a more detailed description of the procedure can be found in the examples which appear hereinafter. It should be understood, however, that the assay method of this invention is not limited to the sandwich ELISA but includes other assay methods, for instance, an agglutination assay which comprises immobilizing G15 antigen and/or G17 antigen on a particulate carrier such as latex particles, gelatin particles, ferrite particles and the like and adding the test sample to a suspension of the particles to see whether agglutination of the particles would take place.

When said sandwich ELISA is employed, the assay sensitivity can be further improved by calculating the difference of the absorbance between the wavelength used for measuring the developed color and the absorbance at a wavelength at which no color is detected. For example, as shown in the examples given hereinafter, when a peroxidase is used as the conjugated enzyme and ABTS (2,2'-Azino-bis(3-ethylbenzothiozoline-6-sulfonic acid) is used as the substrate, the assay sensitivity can be further improved by measuring the differential absorbance between 405 nm and 492 nm, i.e. the subtraction of the absorbance at 405 nm from the absorbance at 492 nm.

It should also be understood that the method of this invention can be carried out using either G15 alone or G17 alone or both concurrently as the antigen. The latter practice is preferred because the assay sensitivity is further improved.

By the method of this invention, anti-Tp antibody can be assayed and the diagnosis of syphilis be made accordingly. The test sample that can be used includes various body fluids, such as serum, from man and other animals requiring a diagnosis of syphilis and appropriate dilutions thereof.

In accordance with this invention, anti-Tp antibody can be assayed with improved sensitivity as compared with any of the hitherto-proposed techniques.

EXAMPLES

The following examples are intended to describe this invention in further detail. It should, of course, be understood that this invention is by no means limited to these specific examples.

Reference Example 1

Preparation of G15 and G17 antigens

*Treponema pallidum* was purified from a rabbit testis in which Tp was innoculated and cultured and the genomic DNA was extracted. Using this as a template as well as the primers prepared based on the known DNA sequence using a DNA synthesizer, DNA fragments corresponding to 15 k and 17 k antigens were prepared by the PCB method. Each of these DNA fragments did not include the 5'-end DNA sequence corresponding to the N-terminal peptide cleaved off in the native antigen. Into the vector pWG6A constructed for expression of GST-fused protein, these DNA fragments were respectively inserted and the resulting vectors were named pWG6A-15 k and pwG6A-17 k, respectively. Each of them was introduced into *Escherichia coli* to induce the expression of G15 or G17 antigen. After expression of the antigen, the *E. coli* was sonicated and centrifuged and the supernatant was serially purified by DEAE-Sepharose (Whatman DE52) ion exchange chromatography and phenyl-Sepharose CL4B (Pharmacia) hydrophobic chromatography. The final yields of G15 and G17 antigens from 1-liter cultures were approximately 60 mg and their purities were not less than 95%. Each of the resulting G15 and G17 antigens was subjected to SDS-polyacrylamide electrophoresis and further to Western blotting using rabbit anti-Tp serum as a primary antibody, whereupon an intense color was developed. On the other hand, *Treponema pallidum* purified from rabbit testis was subjected to SDS-polyacrylamide electrophoresis and to Western blotting using the anti-G15 and anti-G17 monoclonal antibodies constructed by sensitizing mice with G15 and G17 antigens, respectively, as primary antibodies. As a consequence, an intense color developed with the respective native 15 k antigen and 17 k antigen, indicating that immunologically the recombinant G15 and G17 antigens were equivalent to the native antigens 15 k and 17 k.

Example 1

In the wells of a plastic plate (Falcon 39 Micro Test 111 Flexible assay plate), the G15 antigen or G17 antigen prepared in Reference Example 1 was immobilized at various sensitizing concentrations. As control, 47C$_4$ antigen (Amino acid number 1, Met to 434, Gln), a Tp membrane antigen having a molecular weight of 47 kDa, was prepared in accordance with the method of Norgard et al. (INFECTION AND IMMUNITY Apr. 1992, pp. 1568–1576), purified by electrophoresis, and immobilized in the other wells at various sensitizing concentrations. After blocking of the non-specific adhesion sites with 5% Skim Milk, a commercial blocking agent, the wells were washed and 50 µl of the test sample was added. The test sample was prepared by diluting a syphilis patient's serum 500-fold with 10 mM PBS containing 1% skim milk and 0.05% Tween 20 (tradename). After addition of the test sample, the plate was incubated at 37° C. for 1.5 hours. The wells were then washed and 50 µl of peroxidase-conjugated anti-human IgG solution was added. The plate was incubated at 37° C. for 1.5 hours and, then, washed. Then, 50 µl of a solution of the color developer ABTS was added and the plate was incubated for 30 minutes. The reaction was stopped with 100 µl of oxalic acid and the absorbances at 405 nm and 492 nm were measured with a spectrophotometer (Titerteck Multiskan Plus). The results are shown in FIG. 2.

Figure 2:
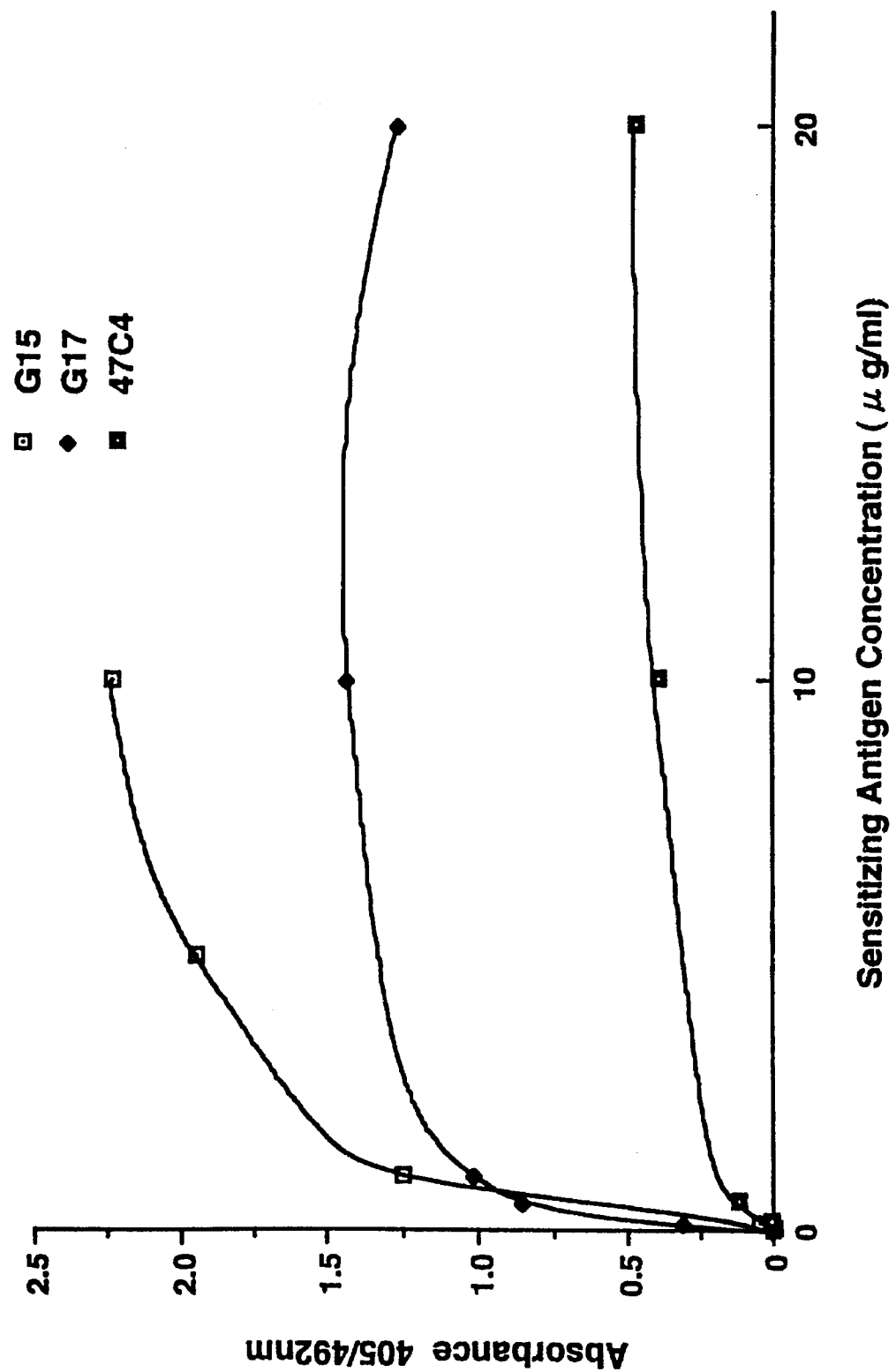
FIG. 2 is a graph showing the results of sandwich ELISA according to the method of this invention using G15 and G17 as antigens in comparison with the results of the comparable assay using $47C_4$.

It can be seen from FIG. 2 that with the absorbance found with the 47C$_4$ antigen being taken as unity, the assay sensitivity at the sensitizing antigen concentration of 10 μg/ml is about 6-fold as high with the G15 antigen arid about 4-fold as high with G17 antigen. Thus, compared with the use of 47C$_4$ antigen, significantly higher assay sensitivities can be obtained with G15 and G17 antigens.

Example 2

Figure 3:
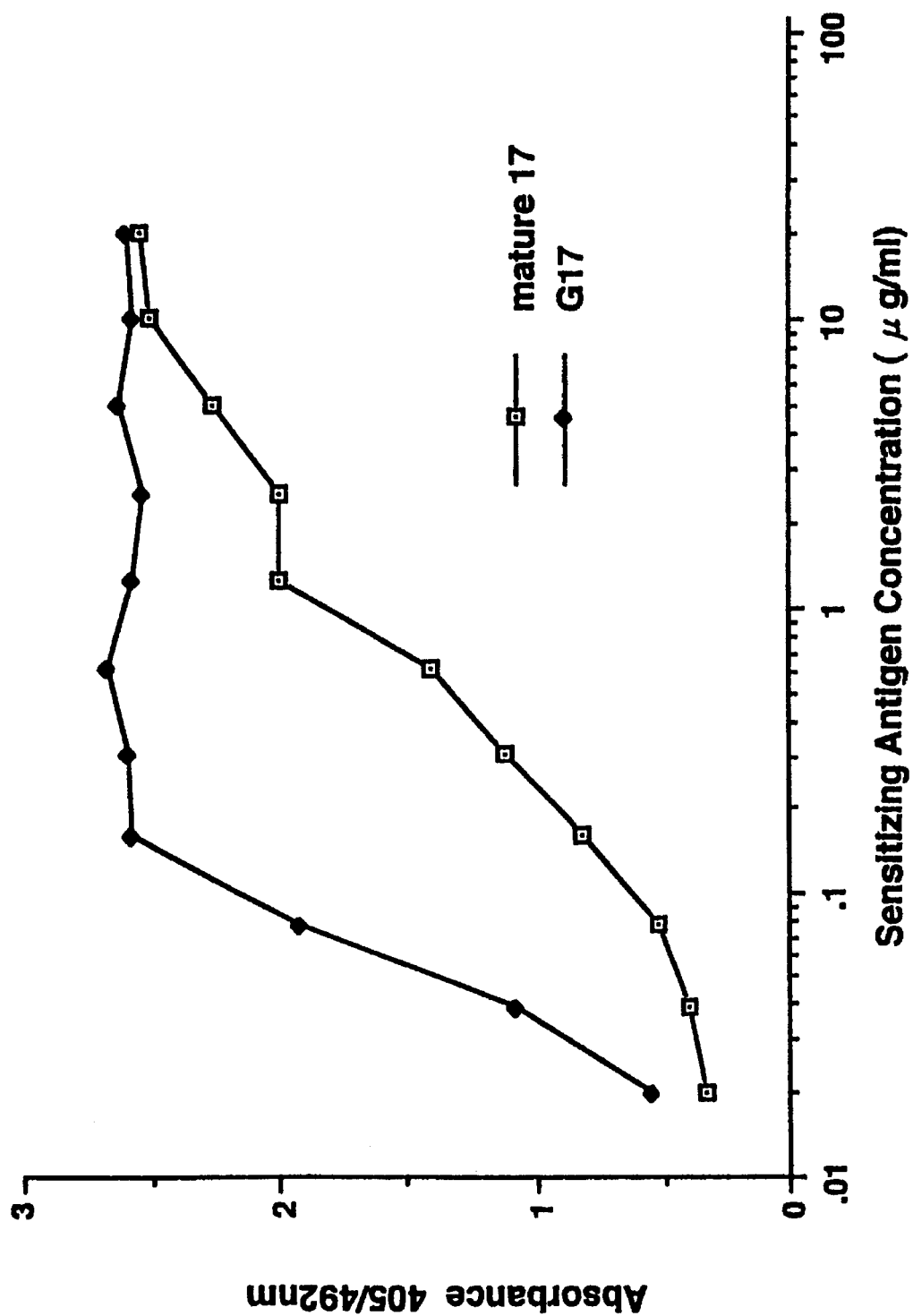
FIG. 3 is a graph showing the results of sandwich ELISA according to the method of this invention using G17 antigen in comparison with the comparable assay using GST-free Mature 7 antigen which was obtained in *E. coli* expression system as a form close to native antigen.

Using the G17 antigen prepared in Reference Example 1 and, as control, the Mature 17 antigen having a molecular weight of 17 kDa (prepared by the method of Norgard et al. (INFECTION AND IMMUNITY, Apr. 1993, pp. 1202–1210) and purified by anion exchange chromatography (DE52) and affinity chromatography using anti-17 k monoclonal antibody), the assay of anti-Tp antibody was carried out in the same manner as Example 1, the results are shown in FIG. 3. It can be seen from FIG. 3 that compared with Mature 17 antigen (Amino acid number 22, Cys to 156, Lys), G17 antigen provided for the half value of maximum absorbance at about one-tenth of the concentration. It was, thus, confirmed that a significantly higher assay sensitivity can be obtained with G17 antigen carrying GST as compared with the corresponding Mature antigen.

Reference Example 2

Assays were carried out in the same manner as in Example 1 using the conventional 47 kDa antigen partially purified (purity≧80%) from Tp (native 47 antigen) by the conventional method and the corresponding recombinant antigen (47C$_2$, Amino acid number 21, Gly to 434, Gln, prepared by the method disclosed in Japanese Kohyo publication Hei-2-500403). The results are shown in FIG. 4.

Figure 4:
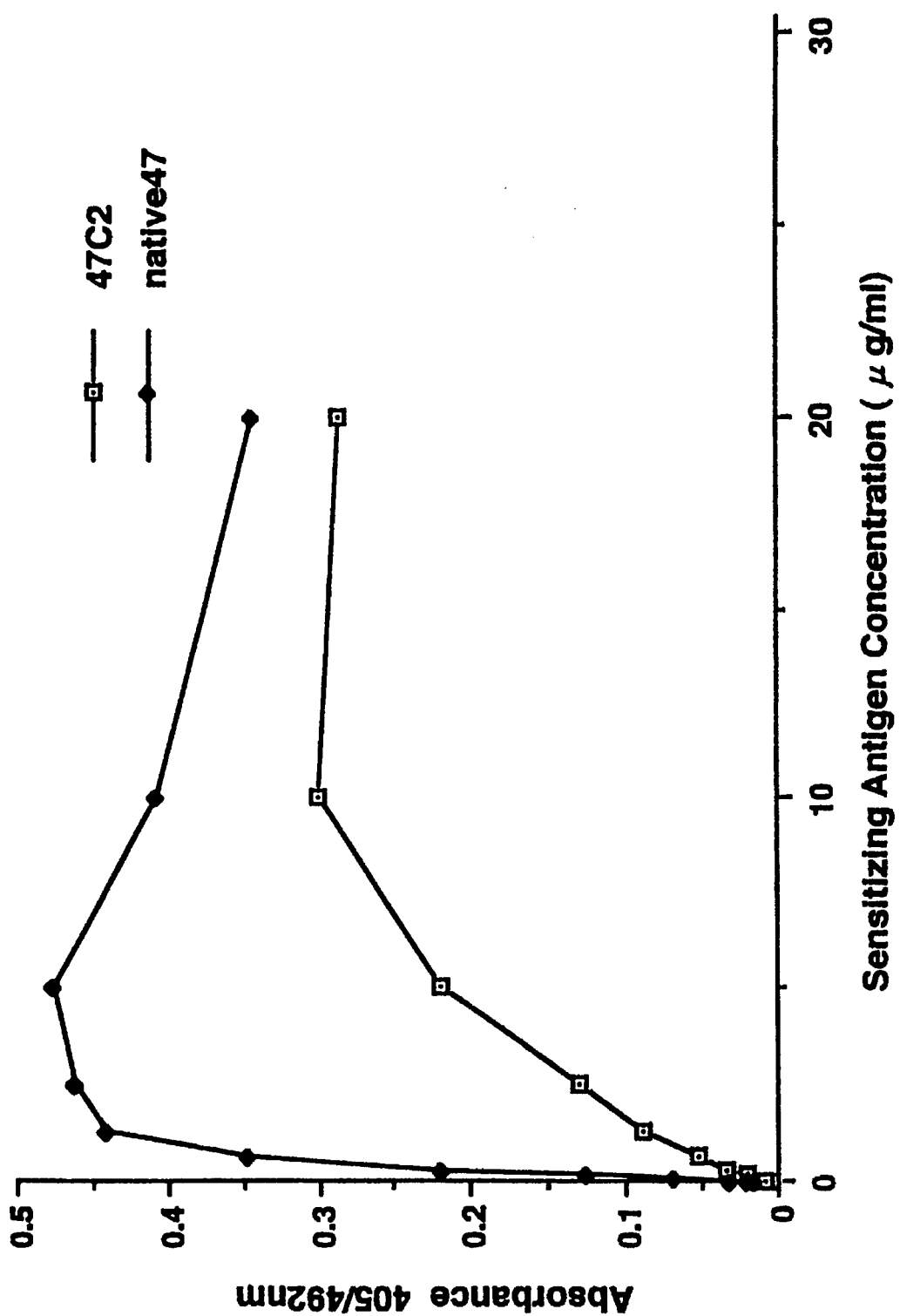
FIG. 4 is a graph showing the results of sandwich ELISA using a recombinant $47C_2$ antigen in comparison with the results of the same assay using native 47 antigen which was purified from Tp innoculated testis.

It is apparent from FIG. 4 that there is no remarkable difference in assay sensitivity between the case of using native 47 and the case of using 47C$_2$, prepared by recombinant DNA technology (although the native 47 was somewhat more sensitive; the vertical scale of FIG. 4 is much different from the scale of FIGS. 2 and 3 with the result that even a minor difference is apparently exaggerated). Comparison of FIG. 4 with FIG. 2 suggests that the sensitivity of the method of this invention employing G15 or G17 antigen is higher than the sensitivity of the conventional method using the native antigen derived from Tp.

Example 3

Using plastic plates whose wells had been sensitized with G15 antigen, G17 antigen, and 47C$_2$ antigen described in Reference Example 2 at a uniform concentration of 10 μg/ml and various dilutions of test serum, the immunoassay was carried out in the same manner as in Example 1. The results are shown in FIG. 5.

Figure 5:
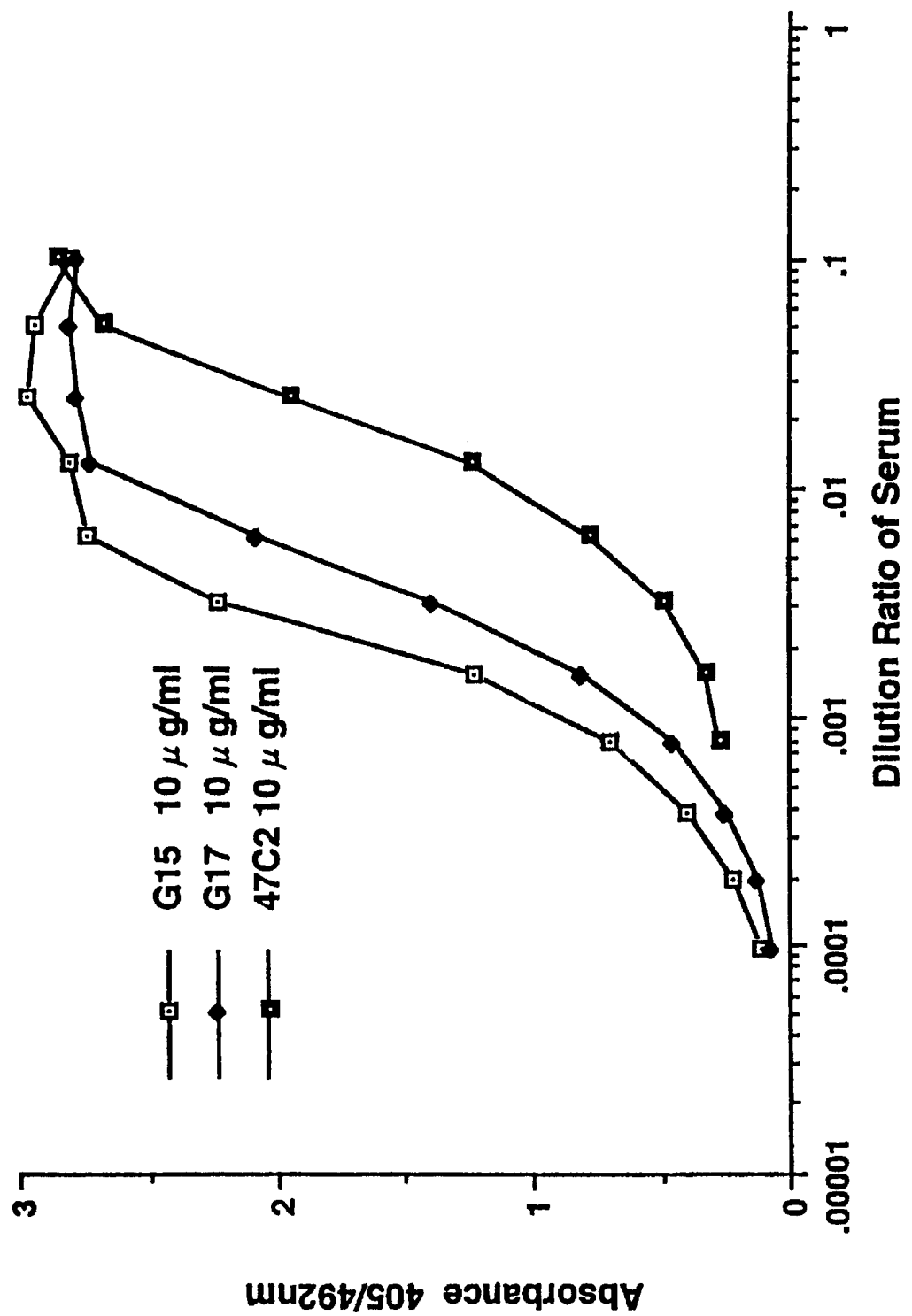
FIG. 5 is a graph showing the results of sandwich ELISA using various dilutions of test serum in accordance with the method of this invention.

It is apparent from FIG. 5 that the amount of serum required for the assay sensitivity equivalent to that of 47C$_2$ antigen was about 1/10 for G15 antigen and about 1/6 for G17 antigen. It was, thus, made clear again that the sensitivity of the method of this invention employing G15 antigen or G17 antigen is higher than the sensitivity of the method using 47C$_2$ as well as native 47K (see FIG. 4).

Reference Example 3

Using 3 kinds of 47 kDa recombinant antigens, namely 47 antigen (Amino acid number 68, Met to 434, Gln, prepared by the method of Norgard et al.(INFECTION AND IMMU-NITY, Apr. 1992, pp. 1568–1576) and purified by hydroxyapatite gel filtration), 47C$_2$ antigen and 47C$_4$ antigen, the wells of plastic plates were sensitized with 5 μg/ml each. Then, using various dilutions of test serum, the assay was performed in the same manner as in Example 1. The results are shown in FIG. 6.

Figure 6:
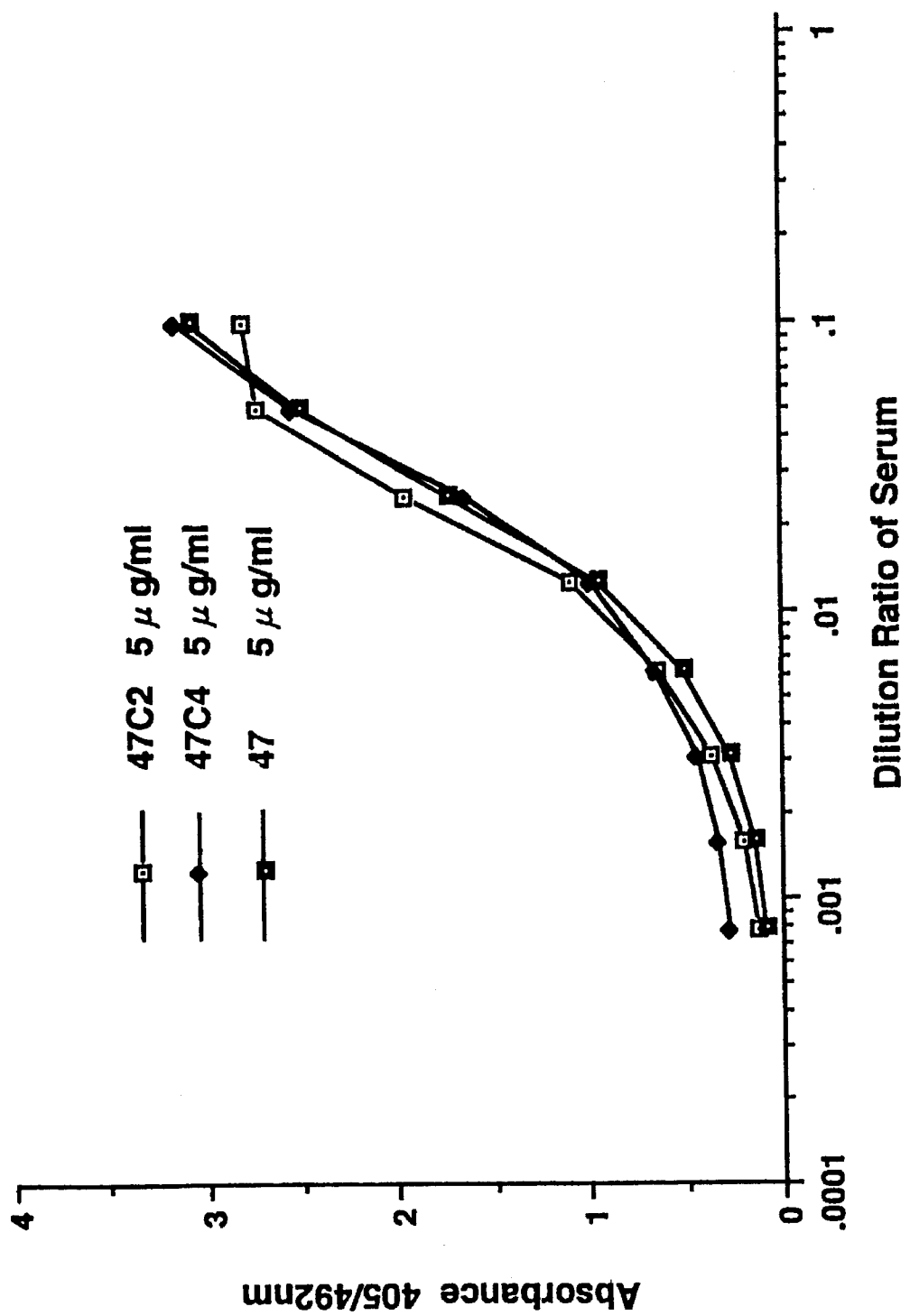
FIG. 6 is a graph showing the results of sandwich ELISA for various dilutions of test serum using 3 kinds of recombinant 47 kDa antigens.

It is apparent from FIG. 6 that there is no remarkable difference in assay sensitivity among these antigens.

In addition, even though a GST fused antigen(G47C$_2$) was used for ELISA, there was no significant difference between G47C$_2$ and 47C$_2$, i.e. the mean value of the ratio between G47C$_2$ and 47C$_2$ was 0.46 ±0.45 (Mean±SD) (n=35 serum samples). Comparison of FIG. 6 with FIGS. 2 and 5 suggests that the method of this invention provides for a higher assay sensitivity than any known 47 kDa antigen.

Example 4

Figure 7:
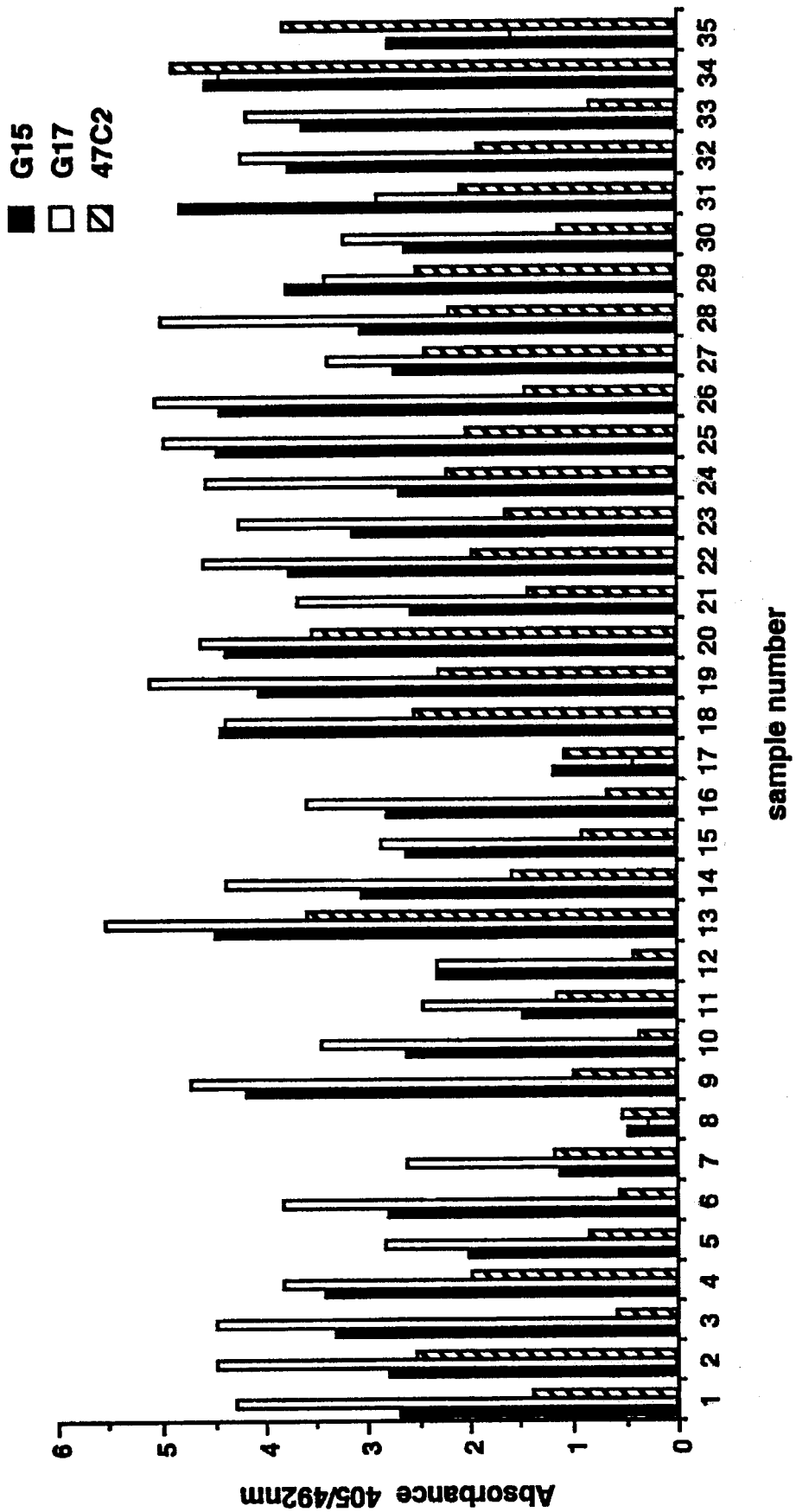
FIG. 7 is a graph showing the results of sandwich ELISA according to the method of this invention in 35 different Tp-positive sera.

Using a plastic plate sensitized with 5 μg/ml of G15 antigen, 1 μg/ml of G17 antigen or 5 μg/ml of 47C$_2$ antigen, 500-fold dilutions of 35 Tp-positive sera (verified to be seropositive by the conventional method) and Tp-negative sera were tested in the same manner as in Example 1. The results are shown in FIG. 7 and Table 1.

TABLE 1

| Sample Number | S/N Ratio | | |
| --- | --- | --- | --- |
| | G15 | G17 | 47C2 |
| 1 | 37.90 | 142.60 | 4.53 |
| 2 | 39.60 | 149.00 | 8.37 |
| 3 | 47.10 | 148.68 | 1.92 |
| 4 | 48.50 | 127.33 | 6.58 |
| 5 | 28.60 | 94.10 | 2.82 |
| 6 | 39.90 | 126.66 | 1.80 |
| 7 | 15.90 | 86.43 | 3.88 |
| 8 | 6.71 | 9.26 | 1.73 |
| 9 | 59.28 | 156.30 | 3.21 |
| 10 | 37.17 | 114.66 | 1.19 |
| 11 | 20.73 | 81.43 | 3.76 |
| 12 | 32.99 | 76.26 | 1.35 |
| 13 | 63.86 | 183.66 | 11.90 |
| 14 | 43.14 | 145.00 | 5.19 |
| 15 | 37.08 | 94.33 | 2.97 |
| 16 | 39.96 | 118.66 | 2.15 |
| 17 | 16.58 | 13.36 | 3.50 |
| 18 | 63.00 | 144.66 | 8.39 |
| 19 | 57.57 | 169.00 | 7.60 |
| 20 | 62.00 | 153.33 | 11.66 |
| 21 | 36.27 | 121.66 | 4.68 |
| 22 | 53.14 | 152.66 | 6.47 |
| 23 | 44.28 | 140.66 | 5.40 |
| 24 | 37.86 | 151.33 | 7.26 |
| 25 | 63.43 | 164.66 | 6.66 |
| 26 | 62.86 | 167.66 | 4.74 |
| 27 | 38.58 | 112.00 | 8.01 |
| 28 | 43.28 | 165.86 | 7.17 |
| 29 | 53.57 | 113.00 | 8.27 |
| 30 | 37.21 | 106.00 | 3.72 |
| 31 | 68.28 | 95.36 | 6.83 |
| 32 | 53.40 | 139.66 | 6.33 |
| 33 | 41.28 | 137.66 | 2.72 |
| 34 | 64.71 | 146.53 | 16.23 |
| 35 | 39.54 | 52.20 | 12.60 |

As can be seen from FIG. 6, the order of response of seropositive cases was G15, G17>>47C$_2$ excepting 3 out of 35 cases. The S/N ratio, i.e. said response (S) divided by response (N) of seronegative cases, is shown as the indicator of relative assay sensitivity in Table 1. The order of S/N ratio was, also, G17, G15>>47C$_2$ and it was confirmed that the use of G15 or G17 antigen provides for significantly higher sensitivity, i.e. about 10-fold (3.1 to 31.2 times) as high in terms of mean G15/47C$_2$ ratio and about 30-fold (3.8 to 96.4 times) as high in terms of G17/47C$_2$ ratio.

---

What is claimed is:

1. A method for quantitative assay of anti-*Treponema pallidum* antibody which comprises assaying anti-*Treponema pallidum* antibody in a sample by immunoanalysis utilizing the antigen-antibody reaction between G15 antigen, which is a protein from the fusion of glutathione-S-transferase to the N-terminal of a *Treponema pallidum* membrane antigen having a molecular weight of 15 kDa, or G17 antigen, which is a protein from the fusion of glutathione-S-transferase to the N-terminal of a *Treponema pallidum* membrane antigen having a molecular weight of 17 kDa or both antigens, and anti-*Treponema pallidum* antibody in the sample, wherein said antigen is present in a limiting amount in said quantitative assay.

2. The method for assay according to claim 1, wherein the assay is performed by enzyme immunoassay using said G15 antigen.

3. The method for assay according to claim 1, wherein the assay is performed by enzyme immunoassay using said G17 antigen.

4. The method for assay according to claim 1, wherein the assay is performed by enzyme immunoassay using said G15 antigen and said G17 antigen.

5. The method for assay according to claim 1, wherein the assay is performed by enzyme immunoassay using said G15 antigen or said G17 antigen or both antigens immobilized on a solid phase.

6. The method for assay according to claim 5, wherein the assay is performed by enzyme immunoassay using said G15 antigen.

7. The method for assay according to claim 5, wherein the assay is performed by enzyme immunoassay using said G17 antigen.

8. The method for assay according to claim 5, wherein the assay is performed by enzyme immunoassay using said G15 antigen and said G17 antigen.

9. The method for assay according to claim 1, wherein the assay is performed by agglutination immunoassay using said G15 antigen or said G17 antigen or both antigens immobilized on a particulate carrier.

10. The method for assay according to claim 9, wherein the assay is performed by agglutination immunoassay using said G 15 antigen.

11. The method for assay according to claim 9, wherein the assay is performed by agglutination immunoassay using said G 17 antigen.

12. The method for assay according to claim 9, wherein the assay is performed by agglutination immunoassay using said G15 antigen and said G17 antigen.

* * * * *